(12) United States Patent
Fuchs

(10) Patent No.: US 12,310,888 B2
(45) Date of Patent: May 27, 2025

(54) ON-THE-FLY TUNING FOR PIEZOELECTRIC ULTRASONIC HANDPIECES

(71) Applicant: JOHNSON & JOHNSON SURGICAL VISION, INC., Irvine, CA (US)

(72) Inventor: Amit Fuchs, Hogla (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 564 days.

(21) Appl. No.: 17/529,713

(22) Filed: Nov. 18, 2021

(65) Prior Publication Data

US 2023/0149213 A1  May 18, 2023

(51) Int. Cl.
*A61F 9/007* (2006.01)
*A61B 17/00* (2006.01)

(52) U.S. Cl.
CPC ........... *A61F 9/00745* (2013.01); *A61B 2017/00725* (2013.01)

(58) Field of Classification Search
None
See application file for complete search history.

(56) References Cited

U.S. PATENT DOCUMENTS

| | | | | |
|---|---|---|---|---|
| 4,056,761 A * | 11/1977 | Jacoby | ................ | B06B 1/0261 331/25 |
| 4,808,948 A * | 2/1989 | Patel | ........................ | H03L 7/02 156/73.2 |
| 5,331,852 A * | 7/1994 | Greiff | ................ | G01C 19/5719 73/862.61 |
| 5,406,503 A * | 4/1995 | Williams, Jr. | ........ | B06B 1/0253 73/579 |
| 5,451,161 A | 9/1995 | Sharp | | |
| 5,581,035 A * | 12/1996 | Greiff | ................... | G01P 15/131 73/514.32 |
| 5,635,739 A * | 6/1997 | Grieff | ................. | G01P 15/0802 73/DIG. 1 |
| 5,646,348 A * | 7/1997 | Greiff | ................... | G01P 15/125 73/514.16 |
| 5,650,568 A * | 7/1997 | Greiff | ................. | G01P 15/0802 73/504.18 |
| 5,739,724 A * | 4/1998 | Alexandre | ............ | B06B 1/0253 318/116 |
| 5,808,396 A | 9/1998 | Boukhny | | |
| 5,817,942 A * | 10/1998 | Greiff | ................... | G01P 15/125 73/514.01 |

(Continued)

FOREIGN PATENT DOCUMENTS

CN  113289880 A  *  8/2021  ............... B06B 3/00

*Primary Examiner* — Jason Lin

(57) ABSTRACT

A method for tuning a phacoemulsification probe during a procedure for treating an eye. The method includes vibrating a piezoelectric actuator of the phacoemulsification probe, by applying to the piezoelectric actuator a tuning signal that (i) covers an operational bandwidth of the phacoemulsification probe and (ii) has an initial power level that is lower than a normal power level set for treating the eye. The tuning signal is measured during an initial signal tuning session. An operating frequency for the phacoemulsification probe is derived from the measured tuning signal. A driving signal, having the normal power level and the derived operating frequency, is applied to the piezoelectric actuator.

20 Claims, 4 Drawing Sheets

(56) References Cited

U.S. PATENT DOCUMENTS

| | | | |
|---|---|---|---|
| 5,852,794 A | 12/1998 | Staggs | |
| 5,938,677 A | 8/1999 | Boukhny et al. | |
| 5,959,390 A | 9/1999 | Boukhny | |
| 6,022,088 A * | 2/2000 | Metzler | A61B 50/15 |
| | | | 312/249.8 |
| 6,028,387 A | 2/2000 | Boukhny | |
| 6,193,683 B1 * | 2/2001 | Ludin | A61F 9/00745 |
| | | | 606/107 |
| 6,324,889 B1 * | 12/2001 | Fluhrer | B06B 1/0261 |
| | | | 73/1.82 |
| 6,626,926 B2 | 9/2003 | Friedman et al. | |
| 6,740,842 B2 * | 5/2004 | Johnson | H05H 1/46 |
| | | | 156/345.45 |
| 6,997,935 B2 | 2/2006 | Anderson et al. | |
| 7,135,029 B2 * | 11/2006 | Makin | A61M 37/0092 |
| | | | 606/171 |
| 7,169,123 B2 * | 1/2007 | Kadziauskas | B06B 1/0253 |
| | | | 606/107 |
| 7,785,336 B2 * | 8/2010 | Staggs | G16H 40/63 |
| | | | 606/169 |
| 7,842,005 B2 * | 11/2010 | Kadziauskas | A61N 7/00 |
| | | | 606/169 |
| 7,871,420 B2 * | 1/2011 | Anderson | A61F 9/00745 |
| | | | 310/317 |
| 9,707,127 B2 | 7/2017 | Kadziauskas et al. | |
| 10,485,699 B2 | 11/2019 | Steen et al. | |
| 11,179,812 B2 * | 11/2021 | Park | B23K 31/125 |
| 2004/0193182 A1 * | 9/2004 | Yaguchi | A61F 9/00745 |
| | | | 606/127 |
| 2009/0124960 A1 * | 5/2009 | Mackool | A61F 9/00745 |
| | | | 606/107 |
| 2021/0330493 A1 | 10/2021 | Steen et al. | |

\* cited by examiner

ON-THE-FLY TUNING FOR PIEZOELECTRIC ULTRASONIC HANDPIECES

FIELD OF THE INVENTION

The present invention relates generally to systems and probes that utilize piezoelectric vibration, and particularly to phacoemulsification systems and probes.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques to vibrate a transducer at a resonant frequency of the transducer were proposed in the patent literature. For example, U.S. Pat. No. 4,808,948 describes an apparatus for periodically sweeping a voltage-controlled oscillator over a range of frequencies which includes a resonant frequency of a transducer being supplied with power by the voltage-controlled oscillator through a power amplifier. The apparatus includes a digital phase detector having a voltage input coupled to the output of the power amplifier and a second voltage input coupled to a current sensor indicative of the phase of the current flowing through the supply circuit of the transducer to provide at the output of the phase detector a voltage signal indicative of phase difference between the voltage and the current in the transducer. The output of the phase detector is coupled to a processor and to the input of a summing circuit. The output of the processor is also coupled to the summing circuit to provide an offset voltage which adjusts the voltage-controlled oscillator to the resonant frequency of the transducer.

As another example, U.S. Pat. No. 5,959,390 describes a system and method for tuning and controlling ultrasonic handpieces by incorporating a broad-spectrum signal as at least a component of the signal used to drive the handpiece. The response of the handpiece to this broad-spectrum signal is measured and the frequency or amplitude or both of the drive signal are adjusted in order to maintain the desired level of handpiece performance. The operation of the systems and the performance of the methods described enables the handpiece to be operated in a most effective manner over a more widely varying range of mechanical load and thermal conditions than was possible through the use of prior control systems and methods.

U.S. Pat. No. 6,626,926 describes how the ability of an ultrasonic system to sweep and lock onto a resonance frequency of a blade subjected to a heavy load at startup is improved by applying a high drive voltage or a high drive current while systematically increasing the level of the applied signal. Increasing the drive signal to the hand piece results in an improved and more pronounced "impedance spectrum." That is, under load, the increased drive signal causes the maximum phase margin to become higher and the minimum/maximum impedance magnitude to become more pronounced. Increasing the excitation drive signal to the hand piece/blade at startup significantly alleviates the limiting factors associated with ultrasonic generators, which results in an increase of the maximum load capability at startup.

SUMMARY OF THE INVENTION

An embodiment of the present invention that is described hereinafter provides a method for tuning a phacoemulsification probe during a procedure for treating an eye. The method includes vibrating a piezoelectric actuator of the phacoemulsification probe, by applying to the piezoelectric actuator a tuning signal that (i) covers an operational bandwidth of the phacoemulsification probe and (ii) has an initial power level that is lower than a normal power level set for treating the eye. The tuning signal is measured during an initial signal tuning session. An operating frequency for the phacoemulsification probe is derived from the measured tuning signal. A driving signal, having the normal power level and the derived operating frequency, is applied to the piezoelectric actuator.

In some embodiments, applying the tuning signal, deriving the operating frequency, and applying the driving signal having the normal power level, are performed uninterruptedly during a treatment session performed by a user.

In some embodiments, applying the tuning signal includes frequency-sweeping a signal across the operational bandwidth.

In an embodiment, deriving the operating frequency includes identifying a time of occurrence of a peak in the measured tuning signal, and determining the frequency of the tuning signal at the time of occurrence of the peak.

In another embodiment, applying the tuning signal includes applying a signal having an instantaneous bandwidth that covers the operational bandwidth.

In some embodiments, deriving the operating frequency includes setting the operating frequency to a resonant frequency of the piezoelectric actuator.

In some embodiments, deriving the operating frequency includes setting the operating frequency to a frequency at which a voltage of the tuning signal has a predefined phase offset relative to a current of the tuning signal.

In an embodiment, applying the driving signal includes running a closed control loop that retains the normal power level.

In some embodiments, applying the driving signal includes running a closed control loop that adapts the operating frequency.

There is additionally provided, in accordance with an embodiment of the present invention, a system for tuning a phacoemulsification probe during a procedure for treating an eye. The system includes a piezoelectric actuator of the phacoemulsification probe and a processor. The piezoelectric actuator is configured to be vibrated by applying to the piezoelectric actuator a tuning signal that (i) covers an operational bandwidth of the phacoemulsification probe and (ii) has an initial power level that is lower than a normal power level set for treating the eye. The processor is configured to (a) measure the tuning signal during an initial signal tuning session, (b) derive, from the measured tuning signal, an operating frequency for the phacoemulsification probe, and (c) apply to the piezoelectric actuator a driving signal having the normal power level and the derived operating frequency.

The present invention will be more fully understood from the following detailed description of the embodiments thereof, taken together with the drawings in which:

DETAILED DESCRIPTION OF EMBODIMENTS

Overview

Figure 1:
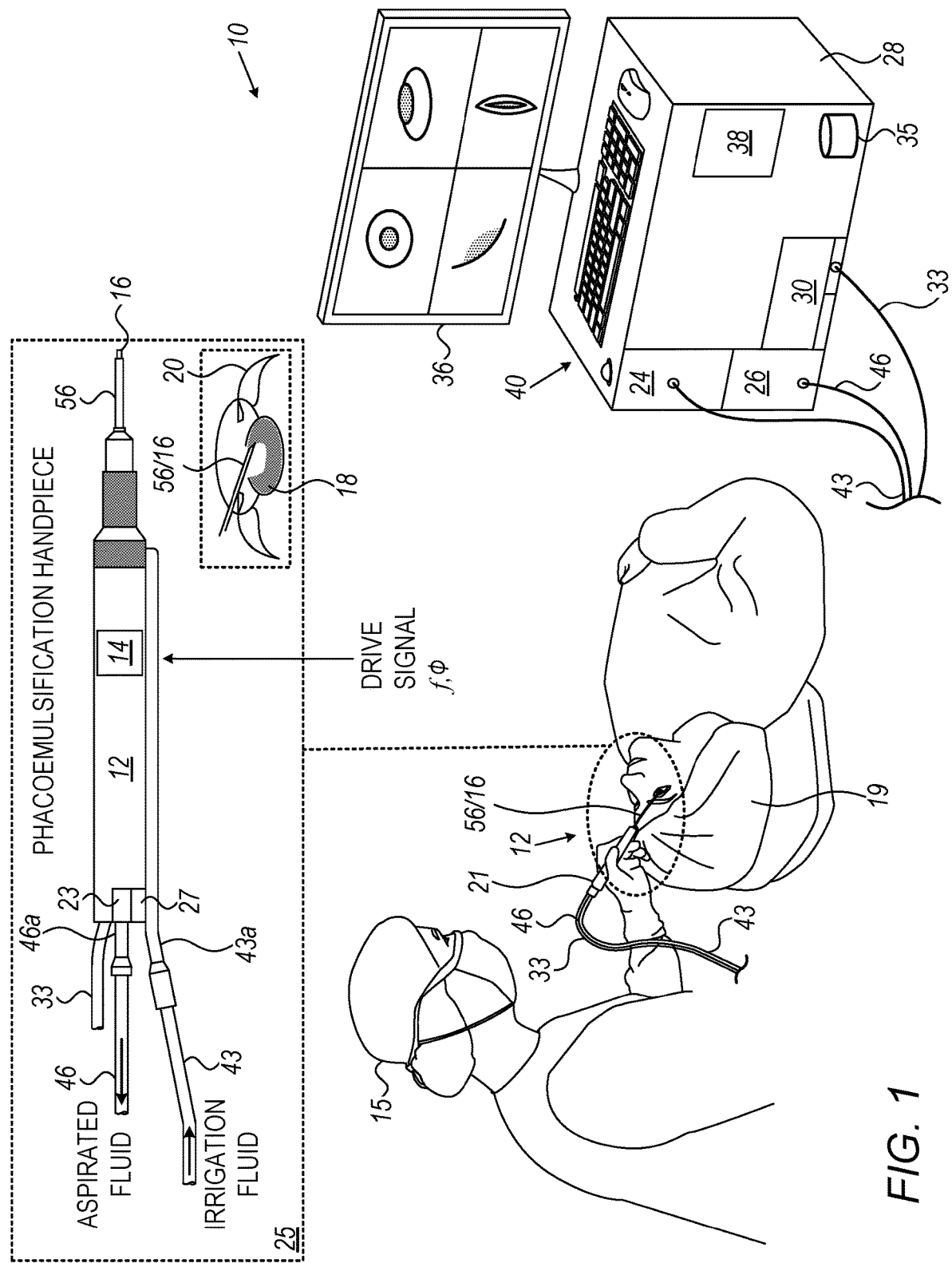
FIG. 1 is a schematic, pictorial view, along with a side view, of a phacoemulsification system, in accordance with an embodiment of the present invention.

A phacoemulsification system typically drives a piezoelectric actuator included in a phacoemulsification probe/handpiece to vibrate a needle of a phacoemulsification probe during a cataract procedure. The piezoelectric actuator of the phacoemulsification probe may be designed to vibrate, in resonance, in a single mode or in multiple modes simultaneously, where each mode has a given "natural" resonant frequency. For example, a multi-resonance mode might yield a complex vibration profile that combines longitudinal, transverse, and torsion vibrations, each with its own resonant frequency. Such a mode may have a complex customizable vibration profile that may allow a physician to better perform phacoemulsification.

Prior to a cataract procedure a phacoemulsification handpiece needs to be tuned. The tuning depends on the type of handpiece, and typically comprises either (i) finding a resonant frequency $f_0$ of a given mode of the piezoelectric actuator of the handpiece, or (ii) finding the frequency where there is a preset phase difference $\Delta\phi$ (for example $-65°$) between the voltage and current being applied at the given mode to the piezoelectric actuator. The tuning typically needs to be repeated prior to every procedure, since there are a large number of varying parameters that affect the frequency, e.g., how tightly the phacoemulsification tip is screwed to the handpiece, which tip is used, and the temperatures of elements of the handpiece.

The tuning gives an initial frequency at which the handpiece is operated. However, since the resonant frequency changes with power, both the power and the frequency during a procedure are monitored and varied separately. A conventional tuning process may take about 30 seconds, which is a considerable amount of time for a phacoemulsification procedure that typically takes on the order of five minutes.

Embodiments of the present invention that are described herein eliminate a separate tuning session by providing an "on-the-fly tuning" technique. In place of a dedicated tuning session, the system is configured so that, on the first activation of the handpiece in a procedure, a very brief, i.e., 50 ms-100 ms, frequency sweep at very low power (e.g., few orders of magnitude lower than a normal power level set for treating the eye) is performed. Performing the frequency sweep typically involves applying to the piezoelectric actuator a tuning signal that (i) covers an operational bandwidth of the phacoemulsification probe and (ii) has an initial power level that is lower than a normal power level set (e.g., lower than the power range provided by the system that a user can select from) for treating the eye. This short frequency sweep is sufficient for a processor driving the handpiece to determine a required initial resonant frequency $f^{0i}$ by measuring the tuning signal (typically measuring a peak in the electrical current or voltage of the tuning signal). $f^{0i}$ is the frequency where an "objective" metric (e.g., minimum measured admittance) is achieved. In a typical case, $f^{0i}$ is the frequency where the real impedance is smallest (admittance is largest), or where the real power highest, assuming voltage amplitude is fixed during the sweep. The duration of such a tuning process is short enough so that it is unnoticeable to the surgeon activating the handpiece.

An alternative to frequency-sweeping is for the processor to apply another type of initial waveform to the piezoelectric actuator over the given frequency range as driving signals, which determines the resonant frequency. For example, the processor may apply wide-bandwidth waveforms having a bandwidth of at least the given frequency range.

From the sweep (or from wide-bandwidth signal), the processor determines an initial resonant frequency, $f^{0i}$, corresponding, for example, to a measured peak in the initial power or peak in real admittance (identified by the processor during the sweep). This frequency is then applied with the "full" (e.g., the aforementioned normal) power that the surgeon expects to use. As a result, there is typically a very slight decrease in the frequency, and a small increase in the power, until resonance at the desired power is achieved. In particular, there's typically a difference between $f^{0i}$ found during the sweep and the optimal frequency for higher power levels (and loading conditions, etc.). It may thus take some time duration, for example, one between several milliseconds and several tens of milliseconds, to find the optimal frequency on the first drastic change in requested power. The processor uses a feedback loop to ensure that the power is kept approximately constant at a nominal value. At the power level requested by the user (the surgeon), the control loop may perform larger adjustments since power is very sensitive to changes in frequency when approaching resonance.

In an embodiment, separate processors and feedback loops are used to ensure that the frequency is at resonance and the power is nominal and stable. The frequency is optimal for a given "objective" of the disclosed algorithm, e.g., frequency of highest real admittance. Considering that exact peak resonance frequency may not be always physically achievable, the controller still tracks the optimal frequency (e.g., with some detuning effectively occurring).

In an embodiment, one or more processor-controlled drive modules are used to independently drive each of the one or more resonant-frequency modes of vibration. A processing circuitry controls each driving oscillator circuitry comprised in the drive module to oscillate in resonance with a piezoelectric crystal mode that it drives. Each of the separate drive modules may be realized in hardware or software, for example in a proportional-integral-derivative (PID) control architecture. The different frequencies of the drive signals are tuned independently of the others, using the disclosed technique, to enable continuous vibration of the piezoelectric actuator at the selected multimode resonant mode.

In another embodiment, while driving the vibration, the drive modules modify the driving signal frequencies to follow the actuator's varying resonant frequencies by minimizing feedback signals. For example, in response to the different drive signals, a measured phase difference is minimized between different voltages across the piezoelectric actuator and respective currents flowing through the piezoelectric actuator. More formally, each module measures a phase difference, $\Delta\phi$, between the driving voltage V and the resulting current I outputted by the driving oscillator, and then minimizes $\Delta\phi$ to maintain the oscillator driving the crystal mode in a resonance frequency into which it was tuned using the disclosed on-the-fly tuning technique. As noted above, another control mode is provided, that seeks to maximize admittance (minimize impedance) of the crystal.

System Description

FIG. 1 is a schematic, pictorial view, along with a side view, of a phacoemulsification system 10, in accordance with an embodiment of the present invention.

As seen in the pictorial view of phacoemulsification system 10, and in inset 25, phacoemulsification probe 12 (e.g., a handpiece 12) comprises a needle 16 surrounded by an irrigation sleeve 56. Needle 16 is hollow and its lumen is used as an aspiration channel.

Needle 16 is configured for insertion into a lens capsule 18 of an eye 20 of a patient 19 by a physician 15 to remove a cataract. The needle (and irrigation sleeve 56) are shown in inset 25 as a straight object. However, any suitable needle may be used with phacoemulsification probe 12, for example, a curved or bent tip needle commercially available from Johnson & Johnson Surgical Vision, Inc., Santa Ana, CA, USA.

In the shown example, probe 12 includes a sensor 27 coupled with irrigation channel 43a, and a sensor 23 coupled with aspiration channel 46a. Channels 43a and 46a are coupled respectively to irrigation line 43 and aspiration line 46. The sensor measurements (e.g., pressure, vacuum, and/or flow) are taken close to the proximal end of the handpiece where the irrigation outlet and the aspiration inlet are located, so as to provide processor 38 an accurate indication of the actual measurements occurring within an eye and provide a short response time to a control loop comprised in processor 38.

As shown, during the phacoemulsification procedure, processor-controlled pump 24 comprised in a console 28 pumps irrigation fluid from an irrigation reservoir (not shown) via irrigation sleeve 56 to irrigate the eye. The fluid is pumped via irrigation tubing line 43 running from console 28 to probe 12. Using sensors (e.g., as indicated by sensors 23 and/or 27), processor 38 controls a pump rate of irrigation pump 24 to maintain intraocular pressure within prespecified limits.

Eye fluid and waste matter (e.g., emulsified parts of the cataract) are aspirated via hollow needle 16 to a collection receptacle (not shown) by a processor-controlled aspiration pump 26 also comprised in console 28 and using aspiration tubing line 46 running from probe 12 to console 28. In an embodiment, processor 38 controls an aspiration rate of aspiration pump 26 to maintain intraocular pressure (in case of sub-pressure indicated, for example, by sensor 23) within prespecified limits.

As further shown, phacoemulsification probe 12 includes a piezoelectric actuator 14 coupled to a horn (not shown) that drives needle 16 to vibrate in a resonant vibration mode, having a frequency $f_0$, that is used to break a cataract into small pieces during a phacoemulsification procedure. Console 28 comprises a piezoelectric drive module 30, coupled with the piezoelectric crystal using electrical wiring running in cable 33.

Drive module 30, which includes analog high-power filters/amplifiers/drivers (and has no control circuitry of its own in the shown embodiment) is controlled by a processor 38 that uses the drive signal or a small-amplitude monitoring signal (e.g., at a detuned frequency) via cable 33 and enables a mechanical resonance of actuator 14 to be monitored and followed using a control loop comprised in processor 38, e.g., by the processor adjusting frequency f of a drive signal. As noted above, the frequency f may denote multiple frequencies when multi-resonant phacoemulsification vibration modes are implemented in probe 12. To this end, a single drive module 30 may receive a superposition of several frequencies with different amplitudes and relative phases.

Therefore, processor 38 may convey one or more processor-controlled driving signals, each having frequency f and phase $\phi$ via cable 33 to, for example, maintain needle 16 at maximal vibration amplitude. The drive module may be realized in hardware or software, for example, in a proportional-integral-derivative (PID) control architecture.

In another embodiment, processor 38 is used for GUI, and for sending high-level commands to a drive-module that includes control circuitry to perform the disclosed method.

In the shown embodiment, processor 38 may receive user-based commands via a user interface 40, which may include setting a vibration mode and/or frequency of the piezoelectric crystal, and setting or adjusting an irrigation and/or aspiration rate of the irrigation pump 24 and aspiration pump 26. Processor 38 may receive user-based commands via a user interface 40, which may include needle 16 stroke amplitude settings and turning on irrigation and/or aspiration. In an embodiment, the physician uses a foot pedal (not shown) as a means of control. For example, pedal position one activates only irrigation, pedal position two activates both irrigation and aspiration, and pedal position three adds needle 16 vibration. Additionally, or alternatively, processor 38 may receive the user-based commands from controls located in a handle 21 of probe 12.

In an embodiment, user interface 40 and display 36 may be integrated into a touch screen graphical user interface.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements, which are omitted for clarity of presentation. For example, physician 15 typically performs the procedure using a stereo microscope or magnifying glasses, neither of which are shown. Physician 15 may use other surgical tools in addition to probe 12, which are also not shown in order to maintain clarity and simplicity of presentation.

One-or-More Piezoelectric Resonant System for Phacoemulsification Probe

Figure 2:
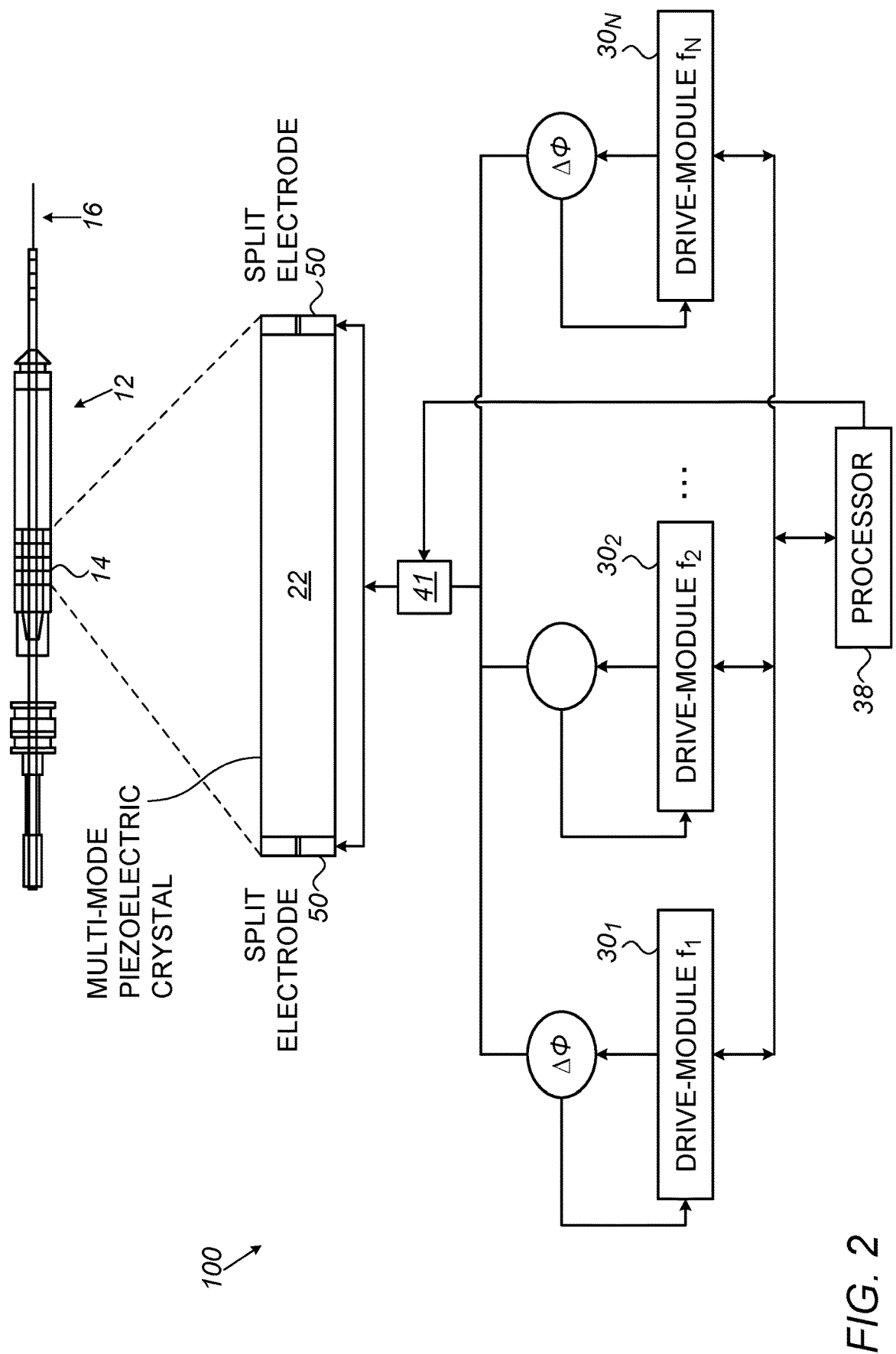
FIG. 2 is a block diagram schematically describing a multi-channel piezoelectric drive system for the phacoemulsification system of FIG. 1, in accordance with an embodiment of the present invention.

FIG. 2 is a block diagram schematically describing a multi-channel piezoelectric drive system 100 for phacoemulsification system 10 of FIG. 1, in accordance with an embodiment of the present invention.

As seen, drive system 100 comprises multi-channel drive-modules $30_1, 30_2, \ldots 30_N$, i.e., N≥1, each coupled to one or more split electrodes 50 of piezoelectric actuator 14 (which may comprise a multi-stack crystal 22) of phacoemulsification probe 12, using electrical links running in cable 33.

Multi-channel drive modules $30_1, 30_2, \ldots 30_N$ are essentially analog units controlled by processor 38 to convey driving signals having resonant frequencies $f_1, f_2, \ldots f_N$ of a multi-resonance mode of piezoelectric actuator 14 to drive modules $30_1, 30_2, \ldots 30_N$. The actuators are controlled by processor 38, by, for example, minimizing detected respective phase differences, $\Delta\phi j$, j=1, 2 ..., N, to keep the complex-mode of the crystal in resonance, e.g., following commands from the processor.

In an alternative embodiment (not shown), the actuators are controlled by processor 38, by, for example, minimizing impedances $z_1, z_2, \ldots z_N$ experienced by the drive system in the multi-resonance mode.

Processor 38 is further configured to connect at least a portion of drive-modules $30_1, 30_2, \ldots 30_N$, using a switching circuitry 41 with different combinations of the one or more multiple-split electrodes 50 of piezoelectric actuator 14, so as to vibrate needle 16 in synchrony in one of several prespecified trajectories.

The example illustration shown in FIG. 2 is chosen purely for the sake of conceptual clarity. FIG. 2 shows only parts relevant to embodiments of the present invention. While FIG. 2 shows a multi-mode/multi-frequency scheme, the invention is just as applicable to phacoemulsification probes driven by a single-mode/single-frequency driving signal (e.g., to a phacoemulsification probes with a single crystal that vibrates in one longitudinal mode).

On-the-Fly Tuning of a Resonant Mode

Figure 3:
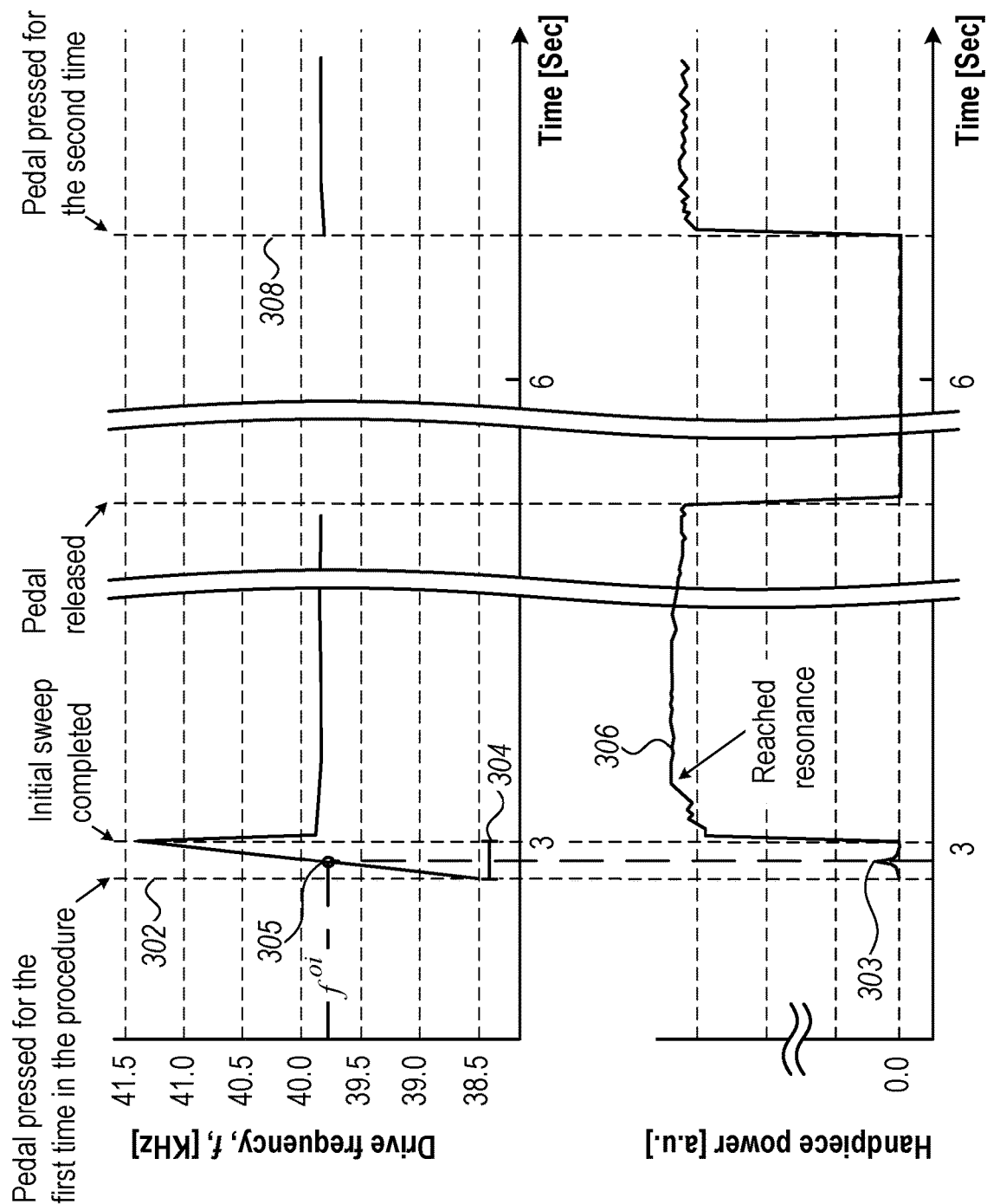
FIG. 3 has graphs of driving frequency and phacoemulsification handpiece power as a function of time, schematically describing an on-the-fly tuning of a resonant mode of probe of FIG. 1, in accordance with an embodiment of the present invention.

FIG. 3 shows graphs of driving frequency and phacoemulsification handpiece power as a function of time, schematically describing an on-the-fly tuning of a resonant mode of probe 12 of FIG. 1, in accordance with an embodiment of the present invention. The disclosed graphs show how deriving the operating frequency comprises identifying a time of occurrence of a peak 303 in the measured tuning signal, and determining a frequency 305 of the tuning signal at the time of occurrence of the peak.

As seen in the driving frequency graph, on a first activation time 302 (e.g., the first time the foot pedal is pressed to activate the power/ultrasound) of handpiece 12 in a procedure, a frequency sweep of the tuning signal is performed for a very brief time duration 304, i.e., 50 ms-100 ms, at very low initial power (as shown in the handpiece power graph). This is sufficient for processor 38, which controls driving of handpiece 12, to determine peak 303 in the low initial power (e.g., a peak in electrical current or in admittance) and determine frequency 305, $f^{Oi}$, required for piezoelectric actuator 14, but the time is short enough so that it is unnoticeable to the surgeon activating the handpiece.

The graphs show the effects if the frequency sought is the resonant frequency. The graph of the driving frequency shows that after initial activation the frequency is swept from 38.5 KHz to 41.5 KHz during a time duration 304 of ~100 ms. The graph of handpiece power shows that a very low power is used during the sweep, and that a peak 303 occurs at that low power. As seen, the processor determines the resonant frequency 305, $f^{Oi}$=39.8 KHz, corresponding to the peak 303 of the power graph. This frequency is then applied with the "full" power that the surgeon expects to use. The graphs further illustrate that there is then a very slight decrease in the frequency, and a small increase in the power, to a peak power 306, until resonance at the desired power is achieved. As noted above, it typically takes slightly longer to find the optimal frequency at high power than at low power and, in parallel, to compensate in the amplitude of the driving signal to maintain the handpiece operating near the desired power.

Just after the initial parameter sweep, the handpiece is already operated very near its optimal parameters and the procedure is performed as usual by the surgeon. Whenever power (308) is reapplied to the handpiece during the procedure, an online tuning algorithm further optimizes the operating conditions of the handpiece, the optimized parameters maintained and automatically improved as needed throughout the procedure.

Figure 4:
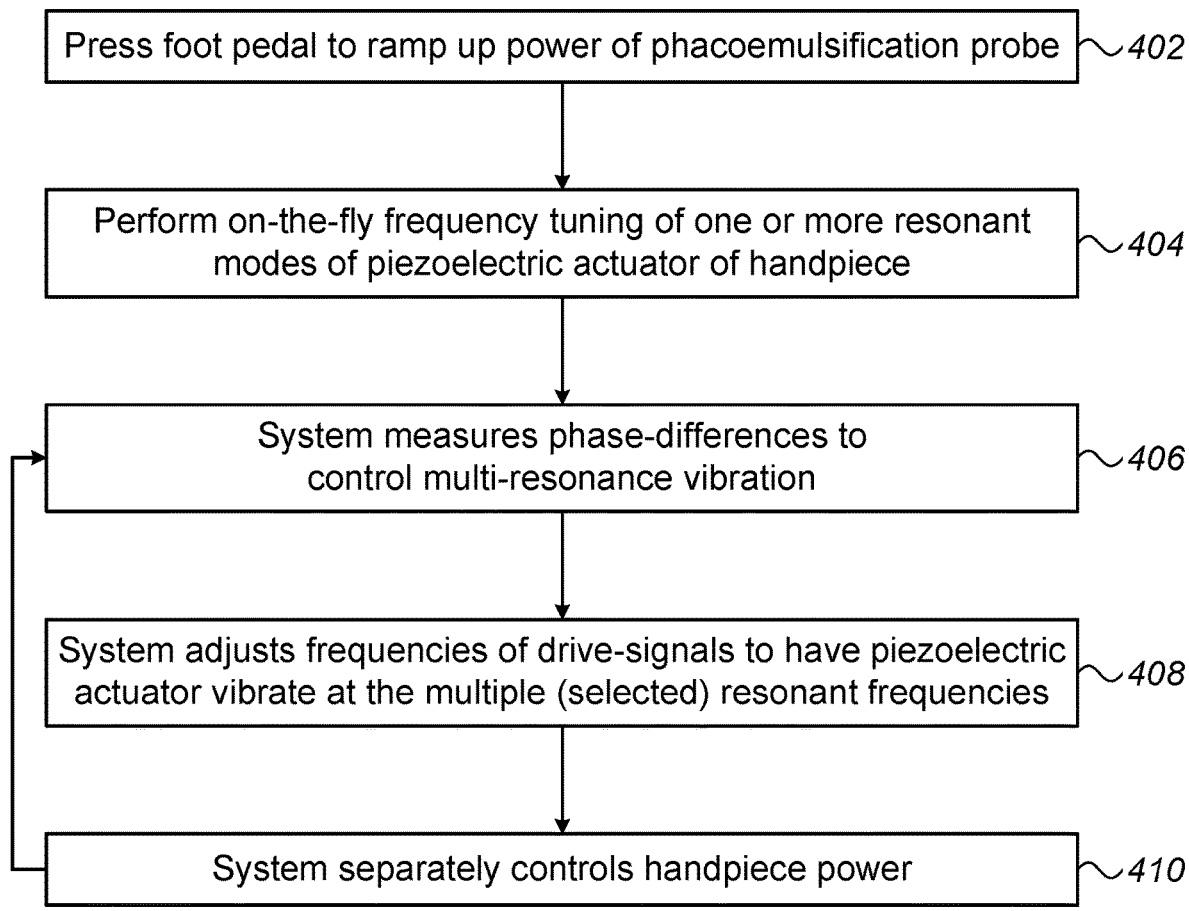
FIG. 4 is a flow chart schematically describing a method for on-the-fly tuning a resonant mode of the phacoemulsification probe of FIG. 1, in accordance with embodiments of the present invention.

FIG. 4 is a flow chart schematically describing a method for on-the-fly tuning of a resonant mode of phacoemulsification probe 12 of FIG. 1, in accordance with embodiments of the present invention. The algorithm, according to the presented embodiment, carries out a process that begins with physician 15 pressing a foot pedal to clinically operate phacoemulsification probe 12. To this end, physician 15 presses a foot pedal to activate the power to the phacoemulsification probe 12 (e.g., presses the foot pedal into a foot position 3 (FP3) and applies power based on the physician selected setting, e.g., panel, linear, desired duty cycle, etc.), at a probe power ramping-up step 402.

During power ramping-up time, the duration of which is typically up to 100 mS, processor 38 performs on-the-fly frequency tuning of one or more resonant modes of piezoelectric actuator 14 inside handpiece 12, at an on-the-fly tuning step 404. The step includes identifying initial peak power 303 (or admittance, in another embodiment) and determining the corresponding frequency 305, $f^{Oi}$.

At a needle vibration controlling step 406, one or more drive modules $30_1, 30_2, \ldots 30_N$ measure the aforementioned phase differences between voltages and currents across and through piezoelectric actuator 14 (e.g., between split electrodes 50).

At a needle motion control step 408, processor 38 of system 10 uses the phase information control step 406 to adjust frequencies of the drive signals such that piezoelectric actuator 14 vibrates at the multiple (selected) resonant frequencies, so as to continue vibrating needle 16 in a complex trajectory.

In a further embodiment, processor 38 uses a separate feedback loop on nominal power (other than that used for tracking a resonant frequency) to ensure that the power is kept approximately constant, at an independent power control step 410. Namely, power control runs in parallel to frequency control (and the two controls may affect each other). As seen, steps 406, 408, 410 are performed continuously while the pedal is pressed during the actual procedure, not just when starting (e.g., also when normal power is applied, to fine tune the frequency). An example of such feedback loop is described above with respect to FIG. 2.

The example flow chart shown in FIG. 4 is chosen purely for the sake of conceptual clarity. For example, additional steps such as irrigating the eye are omitted for simplicity and clarity of presentation.

Although the embodiments described herein mainly address phacoemulsification, the methods and systems described herein can also be used in other applications that may require a multi-channel piezoelectric resonant system to drive a moving member, such as ultrasonic blades, and other types of actuators.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for tuning a phacoemulsification probe during a procedure for treating an eye, the method comprising:
   receiving a signal for activating the phacoemulsification probe for the procedure;
   in response to the signal for activating the phacoemulsification probe for the procedure, applying to a piezoelectric actuator a tuning signal for a tuning time period, wherein the tuning signal covers an operational bandwidth of the phacoemulsification probe and has a power level that is at least fifty percent lower than a normal power level set for treating the eye;
   measuring the tuning signal during the tuning time period;
   deriving, from the measured tuning signal, an operating frequency for the phacoemulsification probe; and
   applying to the piezoelectric actuator, after the tuning time period, a driving signal having a power level at the normal power level and a frequency at the derived operating frequency.

2. The method according to claim 1, wherein applying the tuning signal, deriving the operating frequency, and applying the driving signal, are performed uninterruptedly during a treatment session performed by a user.

3. The method according to claim 1, wherein applying the tuning signal comprises frequency-sweeping a signal across the operational bandwidth.

4. The method according to claim 3, wherein deriving the operating frequency comprises identifying a time of occurrence of a peak in the measured tuning signal, and determining the frequency of the tuning signal at the time of occurrence of the peak.

5. The method according to claim 1, wherein applying the tuning signal comprises applying a signal having an instantaneous bandwidth that covers the operational bandwidth.

6. The method according to claim 1, wherein deriving the operating frequency comprises setting the operating frequency to a resonant frequency of the piezoelectric actuator.

7. The method according to claim 1, wherein deriving the operating frequency comprises setting the operating frequency to a frequency at which a voltage of the tuning signal has a predefined phase offset relative to a current of the tuning signal.

8. The method according to claim 1, further comprising using a closed control loop to maintain the power level of the driving signal at or near the normal power level.

9. The method according to claim 1, further comprising using a closed control loop to adjust the frequency of the drive signal to the operating frequency.

10. A system for tuning a phacoemulsification probe during a procedure for treating an eye, the system comprising:
    a piezoelectric actuator of the phacoemulsification probe, the piezoelectric actuator is configured to be vibrated in response to signals; and
    a processor, which is configured to:
       in response to a signal for activating the phacoemulsification probe for the procedure, provide to the piezoelectric actuator a tuning signal for a tuning time period, wherein the tuning signal covers an operational bandwidth of the phacoemulsification probe and has a power level that is at least fifty percent lower than a normal power level set for treating the eye;
       determine measurements of the tuning signal during the tuning time period;
       derive, from the measured tuning signal, an operating frequency for the phacoemulsification probe; and
       provide, after the tuning time period, to the piezoelectric actuator a driving signal having a power level at the normal power level and a frequency at the derived operating frequency.

11. The system according to claim 10, wherein the processor is configured to provide the tuning signal, derive the operating frequency, and provide the driving signal, uninterruptedly during a treatment session performed by a user.

12. The system according to claim 10, wherein the tuning signal is applied to the piezoelectric actuator by frequency-sweeping a signal across the operational bandwidth.

13. The system according to claim 12, wherein the processor is configured to derive the operating frequency by identifying a time of occurrence of a peak in the measured tuning signal, and determining the frequency of the tuning signal at the time of occurrence of the peak.

14. The system according to claim 10, wherein the tuning signal is applied to the piezoelectric actuator, wherein the tuning signal further comprises a signal having an instantaneous bandwidth that covers the operational bandwidth.

15. The system according to claim 10, wherein the processor is configured to derive the operating frequency by setting the operating frequency to a resonant frequency of the piezoelectric actuator.

16. The system according to claim 10, wherein the processor is configured to derive the operating frequency by setting the operating frequency to a frequency at which a voltage of the tuning signal has a predefined phase offset relative to a current of the tuning signal.

17. The system according to claim 10, further comprising a closed control loop configured to maintain the power level of the driving signal at the normal power level.

18. The system according to claim 10, further comprising a closed control loop configured to adjust the operating frequency of the drive signal.

19. The system according to claim 10, wherein the power level of the tuning signal is at least a few orders of magnitude lower than the normal power level.

20. The system according to claim 10, wherein the normal power level is selected by a user, wherein the power level of the tuning signal is lower than a power range selectable by a user for a surgical procedure, wherein the tuning time period is between 50 ms and 100 ms, and wherein the operation frequency is ascertained each time the phacoemulsification probe is activated for a particular procedure.

* * * * *